(12) United States Patent
Ledo (10) Patent No.: US 8,518,003 B2
(45) Date of Patent: Aug. 27, 2013

(54) SANITARY WASTE DISPOSAL APPARATUS AND METHOD

(76) Inventor: Gregory J. Ledo, Woodbury, MN (US)

(*) Notice: Subject to any disclaimer, the term of this patent is extended or adjusted under 35 U.S.C. 154(b) by 684 days.

(21) Appl. No.: 12/284,643

(22) Filed: Sep. 24, 2008

(65) Prior Publication Data

US 2009/0077734 A1  Mar. 26, 2009

Related U.S. Application Data

(60) Provisional application No. 60/995,092, filed on Sep. 24, 2007.

(51) Int. Cl.
*A61M 1/00* (2006.01)

(52) U.S. Cl.
USPC ........... 604/327; 604/317; 604/323; 604/324; 604/326; 604/331; 604/332; 604/333; 604/337; 604/338; 604/339; 604/341; 604/350; 604/355

(58) Field of Classification Search
USPC ................................ 604/323, 324, 326, 327
See application file for complete search history.

(56) References Cited

U.S. PATENT DOCUMENTS

| | | | |
|---|---|---|---|
| 1,246,791 A | 11/1917 | Salati | |
| 1,342,715 A | 6/1920 | Howe | |
| 1,419,947 A | 6/1922 | Schouten | |
| 1,482,073 A | 1/1924 | Ferdinand | |
| 1,650,365 A | 11/1927 | Kuhn | |
| 2,472,186 A * | 6/1949 | Arnold | 119/869 |
| 2,631,699 A | 3/1953 | Schultz | |
| 2,801,426 A | 8/1957 | Gorce et al. | |
| 2,866,980 A | 1/1959 | Huntington | |
| 2,893,017 A | 7/1959 | Beck | |
| 2,974,321 A | 3/1961 | Salka | |
| 3,063,061 A | 11/1962 | Bertram | |
| 3,142,847 A | 8/1964 | Kurrels | |
| 3,484,875 A | 12/1969 | Eisenberg | |
| 3,643,266 A | 2/1972 | Black | |
| 3,651,810 A * | 3/1972 | Ormerod | 604/329 |
| 3,683,426 A | 8/1972 | Lagstrom | |
| 3,737,920 A | 6/1973 | Savee | |
| 3,950,794 A | 4/1976 | Dalton | |
| 4,710,989 A | 12/1987 | Grenthe | |
| 4,917,692 A * | 4/1990 | Steer et al. | 604/355 |
| 4,938,608 A * | 7/1990 | Espinosa | 383/7 |
| 5,088,134 A | 2/1992 | Douglas | |
| 5,482,376 A * | 1/1996 | Moseley et al. | 383/209 |
| 5,611,092 A | 3/1997 | Van Dusen | |
| 5,958,334 A * | 9/1999 | Haddon | 422/5 |

(Continued)

*Primary Examiner* — Tatyana Zalukaeva
*Assistant Examiner* — Ilya Treyger
(74) *Attorney, Agent, or Firm* — Schroeder & Siegfried P.A.

(57) ABSTRACT

A personal disposable sanitary toilet system including a primary containment bag and a secondary containment bag formed of sheet-like liquid impermeable material. The primary containment bag is funnel-shaped with a pair of straps formed in the upper periphery for use in securing the bag around one's waist. The top of the primary containment bag has an extended front portion which is adapted to be passed between the legs and cover the genitals for sanitary, splatterless relief. The lower end provides a waste containment area that may include a hydrophilic compound for absorbing liquid waste and/or effervescent agents and waste control ingredients. The primary bag may be closed and stuffed into the secondary containment bag which is attached to and surrounds the lower end portion of the primary bag. The top edge of the secondary containment bag has a seal that is closed after the primary bag has been stuffed inside.

18 Claims, 5 Drawing Sheets

(56) References Cited

U.S. PATENT DOCUMENTS

| | | |
|---|---|---|
| 6,116,780 A | 9/2000 | Young et al. |
| 6,341,386 B1 | 1/2002 | Phillips et al. |
| 6,546,569 B2 | 4/2003 | Figueras |
| 6,820,288 B2 | 11/2004 | Suitsu |
| 7,819,850 B2 * | 10/2010 | Mullejans et al. ............ 604/344 |
| 2006/0157995 A1 * | 7/2006 | Cafferty et al. ................ 294/1.5 |

* cited by examiner

SANITARY WASTE DISPOSAL APPARATUS AND METHOD

CROSS REFERENCE TO RELATED APPLICATIONS

This application is an application for a patent which is also disclosed in Provisional Application Ser. No. 60/995,092, filed on Sep. 24, 2007 by the same inventor, namely Gregory John Ledo, and entitled "PERSONAL DISPOSABLE SANITARY TOILET," the benefit of the filing date of which is hereby claimed.

BACKGROUND OF THE INVENTION

The present invention relates generally to portable commodes or toilet systems for use by persons when no permanent toilet facilities are available. More specifically, it pertains to a new waste receptacle bag for receiving urine, feces and other harmful or offensive material for later disposal. The bag requires no support structure in order to be used in a convenient and sanitary manner. The bag contains the waste from start of use until finished with no chance to spill or leak, and consequently soil a person's cloths, or the person.

Portable toilets may be used in locations where no permanent toilet facilities are available, such as outdoor activities or events, outdoor construction or work sites, hunting, emergency response to man-made or natural disasters, travel or where existing toilet facilities are undesirable to use. A typical portable toilet comprises of a generally conventional toilet seat mounted atop a tank, bucket or similar structure, and may be enclosed for privacy. Most portable toilets are large, bulky and heavy, and therefore inconvenient and costly to transport and store. They are expensive to purchase, limited in their disposal options, inconvenient to clean and are subject to residual accumulation of noxious odors and dangerous germs. A need exists for portable toilets that are more economical, more readily transported and stored, do not require cleaning, and minimize noxious odors and the accumulation of dangerous germs.

In partial response to this need, disposable toilets that include a bag-like receptacle, a folded receptacle or similar compact receptacles have been developed. The common concept underlying these toilets is that the bag-like receptacle functions as a liner for collecting waste inside a rigid or collapsible supporting structure. Following use, the receptacle can be removed from the support structure for disposal. Removing the bag-like receptacle from the container leaves it highly susceptible to breakage or tearing, and the resulting discharge of the noxious contents therein. It is also highly likely for the user's hands to become soiled from waste that comes from the neck of these receptacles. Even with the receptacle, the support structure will still need cleaning. It is mentioned in publications that these receptacle-type waste bags can be spread out on the ground for use in emergency situations without the support structure. However, this method is unsanitary, very difficult to use, cumbersome, offensive, and requires very good aim. The user and their trousers are highly likely to become soiled during this process.

Fluid containment bags that can be used by pilots, workers in the field and others who have no immediate access to fixed urinal facilities are also known. These bags are not designed for fecal waste. The above-mentioned bags may or may not include a super absorbent hydrophilic polymer that forms a gel upon contact with urine. These polymer granules may be mixed with fragrances to mask odors, enzymes to break down the urine or biocides to minimize growth of bacteria and or other microorganisms. These polymer granules and mixtures are also being used in some of the toilet receptacle bags described above.

By reviewing the ample prior art on the subject of portable toilets it is apparent that people have long sought a means to effectively and simply collect and dispose of human waste in a sanitary manor when no permanent toilet facilities are available. It would be desirable to provide an economical, disposable, degradable or non-degradable personal sanitary toilet for receipt of liquid and solid waste that requires no rigid or collapsible structure in order to be utilized. It would also be desirable that the portable toilet be able to be stored compactly and that the user can seal and readily transport it to a disposal site after use. It would be desirable to do this without soiling themselves or their clothing, and without experiencing the unpleasant and unsanitary effects of fluid, vapor or odor leakage. These problems and deficiencies are clearly felt in the art and are solved by the present invention in the manner described below.

BRIEF SUMMARY OF THE INVENTION

The present invention is an improved disposable waste receptacle bag for receiving urine, fecal mater and other harmful or offensive waste and a method for doing so. Unlike other waste receptacle bags it requires no ridged, semi-rigid or collapsible structure for it to be used, although it could be used with most known portable commode structures if one desired. This makes the present invention more convenient, more versatile and allows for more freedom of use.

The present waste receptacle bag is a bag-within-a-bag system. It consists of a primary toilet/containment bag, hereinafter referred to as the primary bag, and a secondary containment bag. The primary bag is meant to be secured around the waist with waist straps, pulled up between one's legs and have the person squat and relieve him/herself. The user's pants or shorts can stay on below the knees because all waste is contained from start to finish within the primary bag with no chance of spilling or soiling one's clothes. When done, one simply closes the primary bag, stuffs it into the secondary containment bag and seals it with the snap-like closure similar to the brand ZIP-LOCK®. It is now ready to be disposed of properly; this is effective, simple and sanitary.

The primary bag is a generally angular or funnel-shaped bag that acts to funnel and contain waste into the containment area at the bottom of the bag. This bag can be sealed with a snap-like closure, wire twist tie, draw tie, tape or any other method known by those skilled in the art. The waist straps could be used to seal the bag and the bag may also be tied in a knot. The primary bag can be used by itself or with the secondary bag, which is the preferred method.

The primary bag may be attached to the secondary containment bag by an adhesive or by heat sealing the bottoms, sides or edges of the two bags together. The secondary containment bag may be of any shape suitable to contain the primary bag, but is preferably rectangular in shape and large enough to hold the primary bag, the evacuated waste, and optional wipes and/or a waste gelling powder. It will be a stronger, more durable, puncture resistant bag that may have regular or wide seams and a single or multiple snap-like closure to securely contain the contents.

This bag-within-a-bag system will help minimize odor, vapor and liquid leakage. The preferred manner of construction is for both bags to be made of a liquid-impermeable, degradable sheet-like material, such as from a single, plural or multi-layer plastic film, which will easily be degraded in a landfill. An optional method would have one or both bags made of a liquid-impermeable, non-degradable sheet-like material, such as from a single, plural or multi-layer plastic film that does not degrade, if longer term storage is desirable. Such bags could, for instance, be constructed of a metallized plastic layered film or from a plastic and aluminum foil laminated film.

The primary bag is designed with a plurality of straps that are attached to or a part of the primary bag and can be tied, held or otherwise secured to the user's body, such as around the waist or to the person's legs. Securing the straps around the waist positions the back of the primary bag above and on the outside of the buttocks, so as to hold the bag open below the anus. The front of the bag can then be pulled through the legs and held in a position to cover the genitals. With the bag in the proper position the user can then squat and evacuate him/herself in a very sanitary and splatter-free manner. In so doing, the urine funnels down the front of the primary bag and into the containment area of the primary and the feces drops straight into the containment area.

In the bottom of the primary containment bag may be a combination of one or more waste-control ingredients, including without limitation, a hydrophilic polymer or other super absorbent material to gel any liquid/urine, a deodorant, biocide and/or enzymes. These ingredients may be combined with a powder carrier and an effervescent agent, such as a mixture of citric acid and sodium bicarbonate. Thus, when liquid, urine, comes in contact with the powder formula, the effervescent action will release the fragrance into the air and bubble the super absorbent material so that it engulfs the solid waste, thereby sealing it so as to help prevent the release of malodor.

After wiping him/herself, the user may remove the primary bag from around their waist, express out the excess air and seal the primary bag with a suitable closure. The primary bag is then stuffed inside the secondary bag where the excess air is expressed out of the secondary bag and it is sealed. This waste bag is now ready for proper disposal.

If more vapor and odor control is needed, such as during hunting, a weekend camping trip or on an extended job site, a reusable degradable or non-degradable odor-proof containment bag of suitable size could be used for containment and transportation of the used secondary bags. This reusable bag could be made out of odor impermeable material and would have a snap like closure, carrying handle and tabs on the sides. The tabs could be used with a belt like device to hold it like a fanny pack around one's waist for ease of transportation.

BRIEF DESCRIPTION OF THE DRAWINGS

These and other objects and advantages of the invention will more fully appear from the following description, made in connection with the accompanying drawings, wherein like reference characters refer to the same or similar parts throughout the several views, and in which.

DETAILED DESCRIPTION OF THE INVENTION

Figures 1, 2, 3:
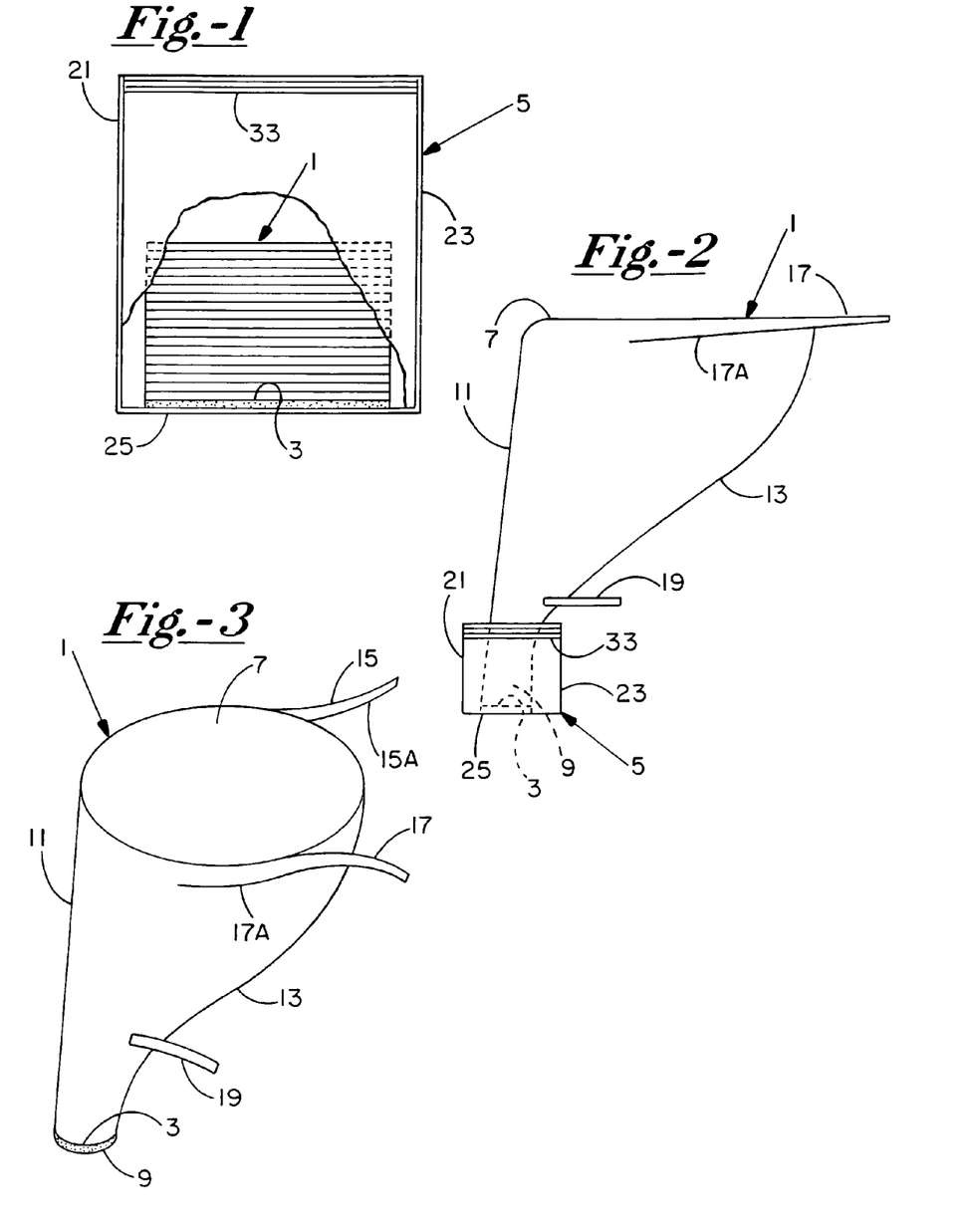
FIG. 1 is a side elevational view of a compact sanitary waste disposal apparatus embodying the principles of my invention, showing the primary containment bag and hydro gel mixture enclosed within the outer secondary containment bag.
FIG. 2 is a side elevational view of the sanitary waste disposal apparatus shown in FIG. 1, with the primary bag attached to the interior of the outer secondary containment bag and extended for use.
FIG. 3 is a perspective view of the primary containment bag, showing the waist straps partially lose from the bag and ready to be secured around the waist of an user.

As shown in FIGS. 1 and 2, the present invention is comprised of a sanitary waste disposal apparatus in the form of compact personal disposable sanitary toilet which requires no ridged, semi-rigid or collapsible structure for it to be used, although it could be used with most known portable commode structures if one desired. The waste disposal apparatus is comprised generally of a primary containment bag 1 with fastening straps 15, 17 and an optional hydrophilic gel mixture 3 contained inside of the primary containment bag 1. As shown in FIG. 1, in a preferred embodiment, the primary bag 1 may be folded or otherwise compacted into smaller compass for storage within a secondary containment bag 5.

As can be seen in FIGS. 2 and 3, when the primary bag 1 is unfolded, it is generally angular or funnel-shaped, having an enlarged open upper end portion 7 and a relatively narrow closed lower end portion 9. The rear side 11 of the primary containment bag 1 between said upper and lower end portions 7 and 9 is generally straight and vertically oriented relative to ground level. By contrast, the front side 13 of the primary containment bag 1 between the upper and lower end portions 7 and 9 thereof bends or curves outwardly away from the rear side 11 to define an extended front end portion, and is generally disposed at an angle relative thereto.

As shown best in FIG. 3, a pair of straps 15 and 17 is secured to opposite lateral sides of the primary containment bag 1 adjacent the upper end portion 7 thereof. These straps 15 and 17 are attached to or a part of the primary bag 1 and are adapted to be tied, held or otherwise secured to the user's body, such as around the user's waist 31, as shown in FIGS. 4-7 of the drawings, or possibly to the user's legs. In a preferred embodiment, these straps 15 and 17 are integrally formed along the upper edge of the primary bag 1, and perforated along lines 15A and 17A, as shown in FIG. 2, for easy tear and release (i.e., readily separable).

One known method for constructing the primary bag 1 is to fold a relatively large panel of sheet-like material in half such that the folded edge forms the rear side 11 of the primary bag 1 and the top edge forms the open upper end portion 7 thereof. The mating edges of material opposite the fold may then be cut generally angularly to the shape of the front side 13 of the primary bag 1, as shown in FIG. 2, and then sealed along the length thereof to form the front side 13 of the bag. The constricted lower portion 9 of the primary bag 1 may then also be sealed to form a closed lower end. The straps 15 and 17 may then be formed by perforating or otherwise weakening the upper end portion 7 of the primary bag 1 along lines 15A and 17A thereof. Of course, other known methods of constructing the primary bag 1 may be implemented without departing from the scope of the invention herein.

In the preferred embodiment shown in FIG. 2, it can be seen that the funnel-like shape of the primary bag 1 helps to draw or funnel waste matter into the narrower containment area at the lower end portion 9 of the bag. The primary bag 1 may also include a separate or integrally attached closure mechanism 19 for sealing the contents therein. This closure mechanism 19 may be in the form of a snap-like closure, wire twist tie, draw tie, tape or any other closure device known by those skilled in the art. The straps 15 and 17 may also be used to seal the bag and/or the bag may be tied in a knot to secure the contents.

Figure 6:
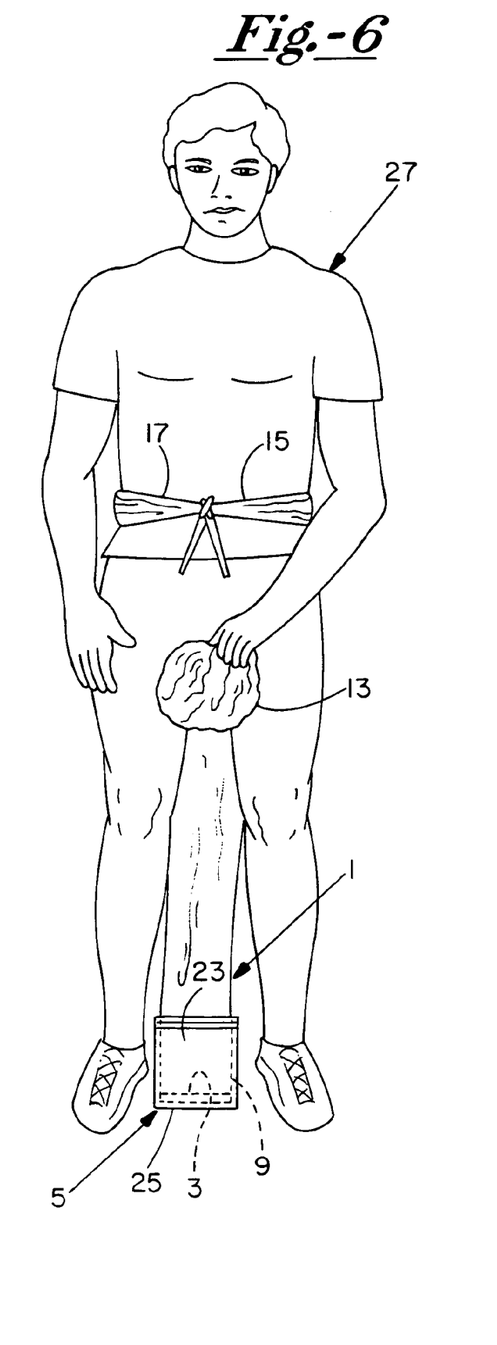
FIG. 6 is a front plan view of the sanitary waste disposal apparatus of FIG. 1, with the primary bag shown tied around the waist of a user and fully deployed for use.
Figure 7:
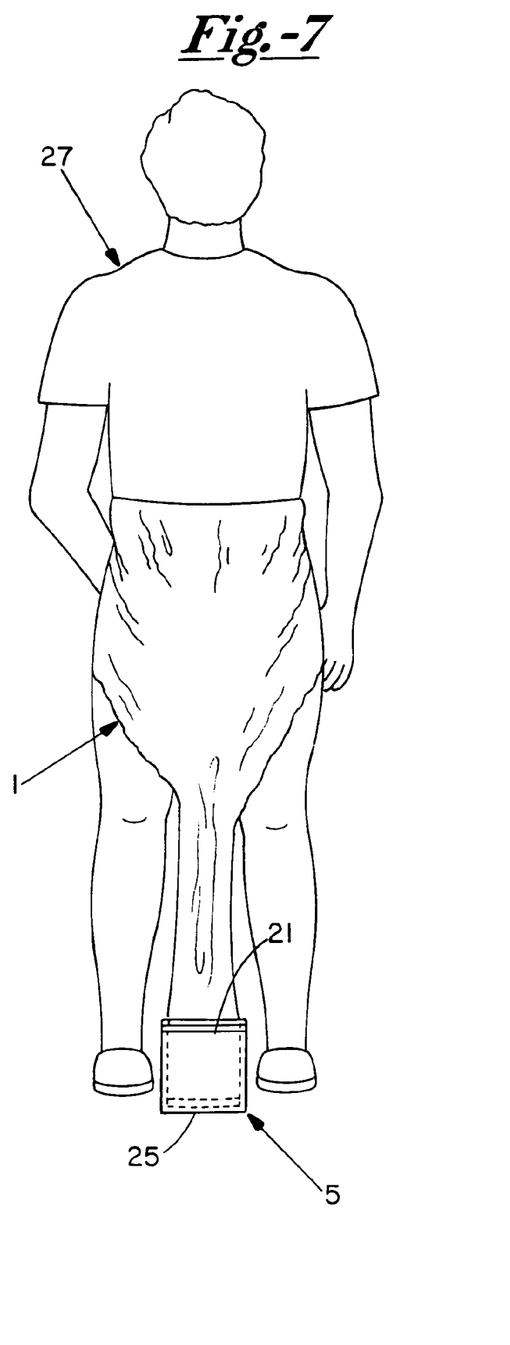
FIG. 7 is a rear plan view of the sanitary waste disposal apparatus of FIG. 1, with the primary bag shown tied around the waist of a user and fully deployed for use.

As noted above, the primary bag 1 can be used by itself or with the secondary bag 5, as shown in FIGS. 1 and 2, which is a preferred embodiment. The embodiment shown in FIG. 2 is essentially a bag-within-a-bag configuration. The primary bag 1 may be attached to the secondary containment bag 5 by means of an adhesive or by heat sealing the bottoms, sides and/or edges of the two bags together. The secondary containment bag 5 may be of any shape suitable to contain the primary bag 1, but is preferably rectangular in shape. As shown in FIG. 2, and in FIGS. 4-7, the secondary containment bag 5 is constructed of small compass relative to the primary containment bag 1 and surrounds only the lower constricted end portion 9 thereof when the primary bag 1 is unfolded and attached to the person's body for use. The primary bag 1 may then be folded and stuffed into the secondary containment bag 5 when use is complete. The two opposite sides 21 and 23, and bottom seam 25 of the secondary containment bag 5 may be constructed with added material to facilitate expansion of the body of the bag, as shown in FIGS. 6 and 7.

The secondary bag 5 is also preferably constructed of a stronger, more durable and puncture resistant material than the primary bag 1. The top of the secondary containment bag 5 is preferably constructed with a double snap type seal 33 to prevent any potential leakage, but could also be sealed by any other suitable means. Besides holding the primary bag 1 with the evacuated waste, the secondary containment bag 5 is preferably constructed of suitable size to hold enough toilet paper for at least one use and an optional disinfecting towelette (not shown) and/or waste-control mixture 3.

It is deemed preferable for both the primary bag 1 and the secondary bag 5 to be made of a liquid-impermeable, degradable sheet-like material, such as from a single, plural or multi-layer biodegradable plastic film, which will easily be degraded in a landfill. Optionally, one or both of the primary and secondary bags 1 and 5 may be made of a liquid-impermeable, non-degradable sheet-like material, such as from a single, plural or multi-layer plastic film that does not degrade, if longer term storage is desirable. A metallized plastic layered film or plastic and aluminum foil laminate could be used as such a non-degradable material, if so desired. Also, it is further contemplated that one or both of the primary and secondary bags 1 and 5 could optionally be made of a material which emits an odor-masking fragrance, such as a scent-impregnated plastic material.

As shown best in FIGS. 1 and 2, in the bottom of the primary containment bag 1 may be a combination of one or more waste-control ingredients 3, including without limitation, a hydrophilic polymer or other super absorbent material to gel any liquid/urine; an odor neutralizer; a deodorant or other fragrance emitting substance to mask the odor; a biocide to minimize growth of bacteria and/or other microorganisms; and/or certain enzymes to help break down the waste material. These ingredients may be combined with a powder carrier and an effervescent agent, such as a mixture of citric acid and sodium bicarbonate. Thus, when the liquid/urine comes in contact with the powder formula, the effervescent action will release the fragrance into the air and bubble the super absorbent material so as to engulf any solid waste, thereby sealing it and helping to prevent the release of malodor.

Figure 4:
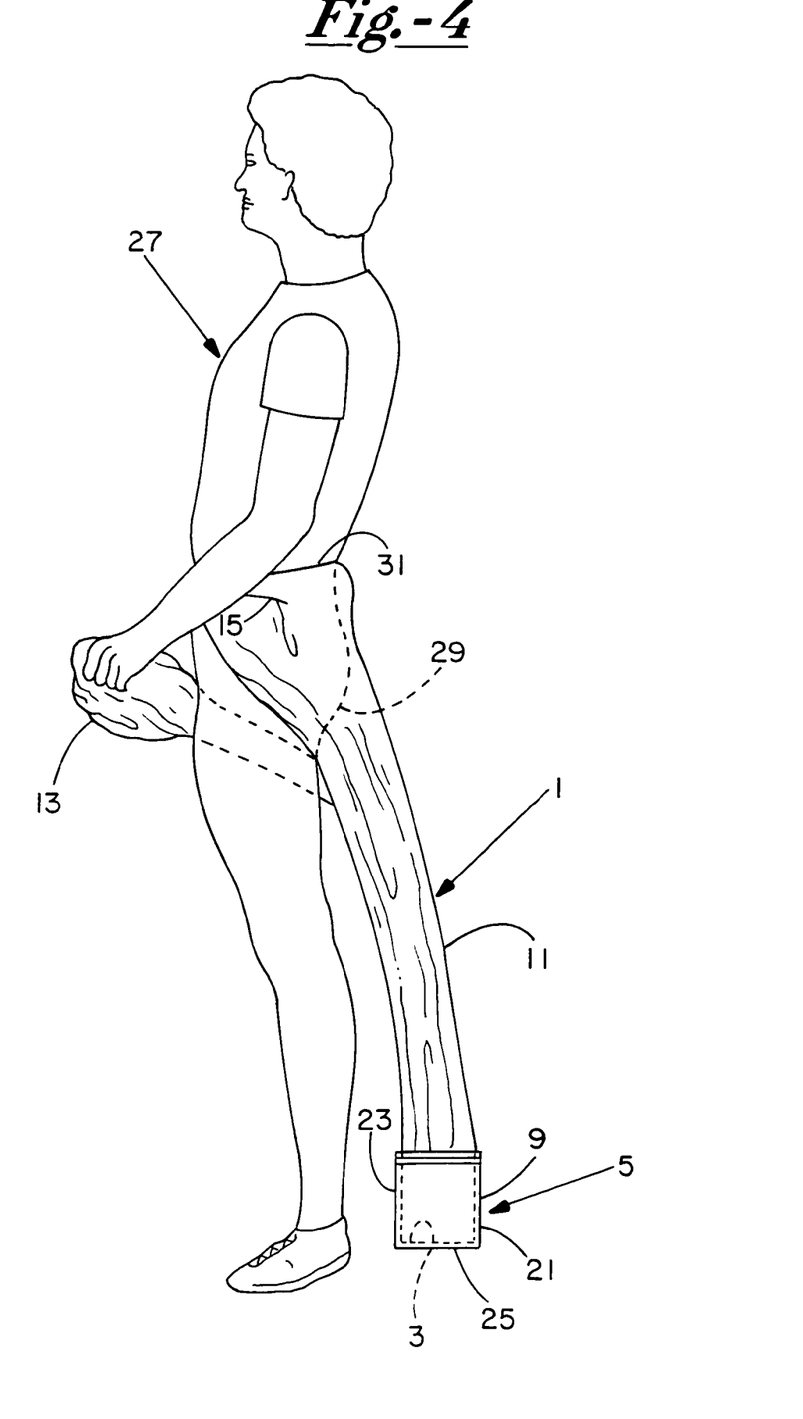
FIG. 4 is a side elevational view of the sanitary waste disposal apparatus of FIG. 1, with the primary bag shown tied around the waist of a user and fully deployed for use.

With reference now being made to FIGS. 4-7, the operation and intended manner of use of the present invention will be explained. FIGS. 4-7 illustrate proper positioning of the sanitary waste disposal apparatus with the primary bag 1 in full deployment and ready for use. As shown in FIG. 4, the primary containment bag 1 is angled away from the user's body 27 as the straps 15, 17 are secured around the user's waist area 31, and one can see how the bag will contain the waste from start to finish. It shows the primary bag 1 attached to the secondary containment bag 5 and the back or rear side 11 of the primary bag 1 positioned above and outside the user's buttocks 29. It also shows the front portion 13 of the bag pulled between the legs of the user and positioned to cover the user's genital region.

Figure 5:
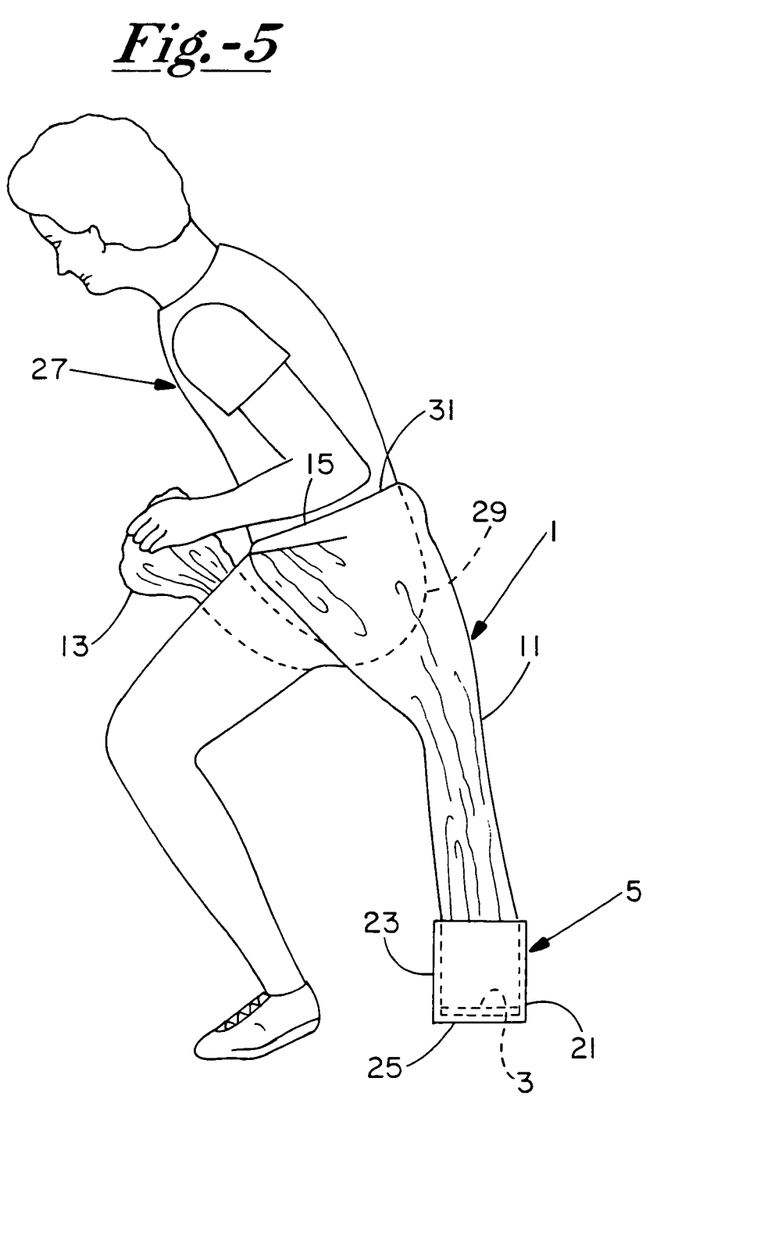
FIG. 5 is a side elevational view of the sanitary waste disposal apparatus of FIG. 1, showing the manner of use thereof.

FIG. 5 illustrates the user in a squatting position, with the primary bag 1 attached to the secondary bag 5 and the back of the primary bag 1 positioned above and outside the user's buttocks 29. It also shows the straps 15, 17 secured around the user's waist 31, and the front portion 13 of the primary bag 1 pulled between the legs and positioned to cover the genital region of the user. By squatting and pulling the front 13 of the primary bag 1 over the genitals, the user will also position their anus above the lower containment area 9 of the bag. This allows the fecal matter to drop directly into the lower containment area 9. When properly positioned, the front of the bag 13 should be slightly billowed out so the urine runs smoothly down the inside front of the bag 1 for a sanitary, non-splattering evacuation of waste.

FIGS. 6 and 7, respectively, show opposite front and rear views of my sanitary waste disposal apparatus in use. As shown, the waist straps 15, 17 are secured around the user's waist 31, with the primary bag 1 pulled through the legs and above the user's genital region. The rear portion of the primary bag 1 is positioned around and above the buttocks and the lower end portion 9 of the primary containment bag 1 is secured to the inside the secondary containment bag 5.

In operation, the secondary containment bag 5 is first opened and the sundries removed. The primary bag 1 is then deployed by pulling it out of the secondary containment bag 5, grasping and opening the top edge of the primary bag 1 and filling it with air. With the primary bag 1 in one hand, it is passed behind the user's back and the straps 15, 17 are grasped in each hand. The primary bag 1 is then positioned above the user's buttocks 29 with the buttocks 29 inside the bag, as shown in FIGS. 4-7. The straps 15, 17 are then brought forward around the waist 31 in front of the user, where they are secured together to hold the primary bag 1 in place.

By reaching between the legs, the front side 13 of the primary bag 1 is grasped and drawn forward, thus bringing it through and between the legs, and covering the user's genital region. After a quick check to verify proper positioning, the user can squat and relieve him/herself. The primary bag 1 can then be removed and the user may wipe clean.

Upon completion, any excess air should be expressed out of the primary containment bag 1 and it should be sealed with an appropriate closure mechanism 19. One way the air can be expressed out of the bag is to start near the lower containment area 9 and twist the bag 1 moving upwards. Once the excess air is out of the primary bag 1, it can be sealed with the appropriate closure 19 and stuffed inside the secondary containment bag 5, which can then be sealed with the appropriate snap-like closure 33. The personal disposable sanitary toilet is now ready for proper disposal.

Figure 8:
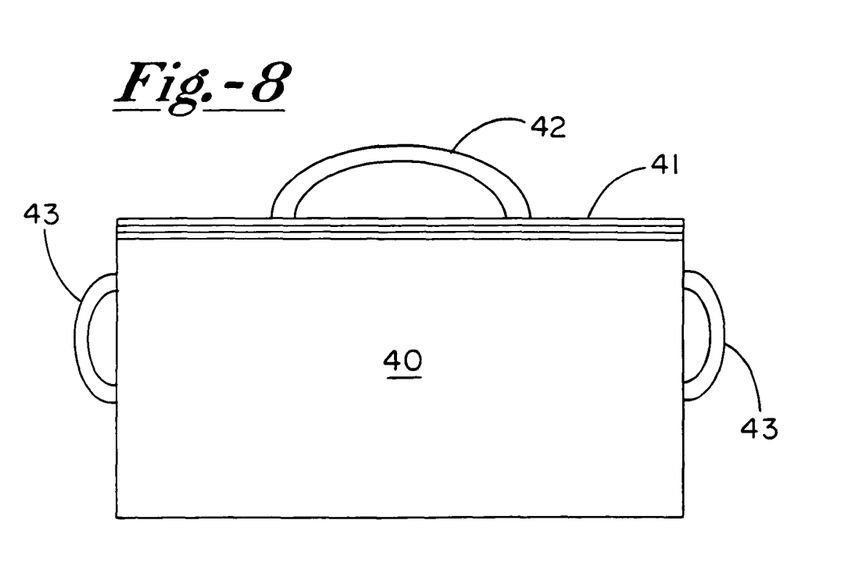
FIG. 8 is a side elevational view of a reusable odor-proof containment and transporting container for storage and transportation of the primary and secondary containment bags once they have been used.

As shown in FIG. 8, if more vapor and odor control is needed, such as during hunting, a weekend camping trip or on an extended job site, a reusable degradable or non-degradable odor-proof containment bag 35 of suitable size could be used for containment and transportation of the used secondary bags 5. This reusable bag 40 could be made out of odor impermeable material known as a metallized vapor barrier film such as a PAKVF2.5MB, manufactured by Impak Corporation, Los Angeles, Calif., which is a 2.5 mil thick multi-layer film comprising a vapor-deposited aluminum barrier layer between polyester and black polyolefin film layers. It could have a snap-like closure mechanism 41, a carrying handle 42 and tabs 43 on the sides. The tabs 43 could be used with a belt-like device in order to hold it like a fanny pack around one's waist 31 for ease of transportation.

It will, of course, be understood that various changes may be made in the form, details, arrangement and proportions of the parts without departing from the scope of the invention which comprises the matter shown and described herein and set forth in the appended claims.

The invention claimed is:

1. A sanitary waste disposal apparatus, comprising:
   (a) a primary containment bag and body attachment member being formed integrally as a unitary structure from a single panel of flexible sheet-like liquid-impermeable material, said primary containment bag being formed in the general shape of a funnel with an open upper end portion, a closed constricted lower end portion and an intermediate wall portion extending between said upper and lower end portion, said open upper end portion having a peripheral edge which is devoid of supporting structure attached thereto;
   (b) said body attachment member coextending with and forming substantially said peripheral edge of said upper end portion of said primary containment bag to facilitate direct attachment of said primary containment bag to the body of a person with the person's buttocks positioned inside said primary containment bag; and
   (c) a secondary containment bag being made of a flexible sheet-like liquid-impermeable material, said secondary containment bag being constructed of small compass relative to said primary containment bag and being attached to and surrounding only said lower constricted portion of said primary containment bag when said primary containment bag is attached to the body of a person, said secondary containment bag being adapted to contain said primary containment bag by folding said primary containment bag therein.

2. The sanitary waste disposal apparatus defined in claim 1, wherein said open upper end portion of said primary containment bag defines an extended front section of sufficient dimensions to be drawn between the person's legs after securing said primary containment bag to the body of the person.

3. The sanitary waste disposal apparatus defined in claim 2, wherein said primary containment bag has a front side and an opposing rear side, said body attachment member being secured to said primary containment bag adjacent said rear side thereof, and said extended front section extending toward said front side thereof.

4. The sanitary waste disposal apparatus defined in claim 1, wherein said body attachment member is comprised of a pair of straps integrally formed with said primary containment bag.

5. The sanitary waste disposal apparatus defined in claim 4, wherein said straps are at least partially attached to said upper end portion of said primary containment bag by a readily separable perforated tear line formed in said primary containment bag.

6. The sanitary waste disposal apparatus defined in claim 4, wherein said primary containment bag has a front side and an opposing rear side, and said integral straps extend in opposite directions around said open upper end portion of said primary containment bag from said rear side of said primary containment bag toward said front side thereof.

7. The sanitary waste disposal apparatus defined in claim 4, wherein said primary containment bag is constructed throughout of a biodegradable material, and said straps are comprised of a top edge section of said upper end portion of said primary containment bag.

8. The sanitary waste disposal apparatus defined in claim 1, including a closure mechanism disposed adjacent said lower end portion of said primary containment bag for closing said primary containment bag after the waste material is discharged therein.

9. The sanitary waste disposal apparatus defined in claim 1, wherein said secondary containment bag has an interior surface to which said lower end portion of said primary containment bag is directly secured.

10. The sanitary waste disposal apparatus defined in claim 1, wherein said secondary containment bag includes an opening for receiving said primary containment bag, and a sealable closure mechanism for sealing said primary containment bag within the confines of said secondary containment bag.

11. The sanitary waste disposal apparatus defined in claim 1, wherein said primary containment bag contains within its interior at least one substance from a group consisting of an absorbent hydrophilic polymer, an odor neutralizer, a fragrance, an enzyme and a biocide.

12. The sanitary waste disposal apparatus defined in claim 11, wherein said primary containment bag contains within its interior an effervescent agent.

13. The sanitary waste disposal apparatus defined in claim 1, wherein said primary containment bag is constructed of a fragrance-emitting material.

14. A sanitary waste disposal apparatus, comprising:
   (a) a primary containment bag and body attachment member being formed integrally as a unitary structure from a single panel of flexible sheet-like biodegradable liquid-impermeable material, said primary containment bag being formed in the general shape of a funnel with an open upper end portion, a closed constricted lower end portion and an intermediate wall portion extending between said upper and lower end portions which forms front, rear and lateral sides to said primary containment bag, said open upper end portion having a peripheral edge which is devoid of supporting structure attached thereto;
   (b) said body attachment member coextending with and forming substantially said peripheral edge of said upper end portion of said primary containment bag to facilitate direct attachment of said primary containment bag to the body of a person with the person's buttocks positioned inside said primary containment bag;
   (c) a secondary containment bag being made of a flexible sheet-like biodegradable liquid-impermeable material, said secondary containment bag having a sealable opening leading to its interior and being adapted to receive and enclose said primary containment bag therein; and
   (d) said secondary containment bag being constructed of small compass relative to said primary containment bag and being attached to and surrounding only said lower constricted portion of said primary containment bag when said primary containment bag is attached to the body of a person, said lower closed end portion of said primary containment bag being affixed directly to the interior of said secondary containment bag and being adapted to contain said primary containment bag by folding said primary containment bag therein.

15. The sanitary waste disposal apparatus defined in claim 14, wherein the dimensions of said upper end portion of said primary containment bag extending between said front and rear side thereof are substantially greater than the dimensions of said lower end portion of said primary containment bag extending between said front and rear side thereof.

16. The sanitary waste disposal apparatus defined in claim 14, wherein said rear side of said primary containment bag between said upper and lower end portions is generally vertically oriented, and said front side of said primary containment bag between said upper and lower end portions is disposed at an angle relative to said rear side thereof.

17. The sanitary waste disposal apparatus defined in claim 14, wherein said upper end portion of said primary containment bag adjacent said front side thereof defines an extended front section of sufficient dimensions to be drawn between the person's legs after securing said primary containment bag to the body of the person.

18. The sanitary waste disposal apparatus defined in claim 14, wherein said primary containment bag contains within its confines an effervescent agent and at least one material taken from a group consisting of an absorbent hydrophilic polymer, an odor neutralizer, a fragrance, an enzyme and a biocide.

* * * * *